(12) United States Patent
Williams et al.

(10) Patent No.: US 7,201,869 B2
(45) Date of Patent: *Apr. 10, 2007

(54) STERILIZER WITH RESTRICTOR

(75) Inventors: Harold R. Williams, San Clemente, CA (US); Szu-Min Lin, Laguna Hills, CA (US); Robert Lukasik, Lake Elsinore, CA (US)

(73) Assignee: Ethicon, Inc., Somerville, NJ (US)

( * ) Notice: Subject to any disclaimer, the term of this patent is extended or adjusted under 35 U.S.C. 154(b) by 444 days.

This patent is subject to a terminal disclaimer.

(21) Appl. No.: 10/186,044

(22) Filed: Jun. 28, 2002

(65) Prior Publication Data

US 2004/0001775 A1    Jan. 1, 2004

(51) Int. Cl.
*A61L 2/20* (2006.01)

(52) U.S. Cl. ............................ 422/28; 422/33; 422/292

(58) Field of Classification Search ............... 422/23, 422/27, 28, 33, 292, 300
See application file for complete search history.

(56) References Cited

U.S. PATENT DOCUMENTS

| | | | |
|---|---|---|---|
| 2,595,539 A * | 5/1952 | Redman, Jr. ............. | 134/56 R |
| 4,643,867 A | 2/1987 | Hornak et al. | |
| 4,704,254 A | 11/1987 | Nichols | |
| 4,744,951 A * | 5/1988 | Cummings et al. ........... | 422/28 |
| 5,633,424 A * | 5/1997 | Graves et al. ................ | 422/22 |
| 5,804,139 A | 9/1998 | Lin et al. | |
| 5,851,485 A | 12/1998 | Lin et al. | |
| 5,961,921 A | 10/1999 | Addy et al. | |
| 6,030,579 A | 2/2000 | Addy et al. | |
| 6,106,772 A | 8/2000 | Kohler et al. | |
| 6,325,972 B1 * | 12/2001 | Jacobs et al. ................. | 422/33 |
| 6,365,102 B1 | 4/2002 | Wu et al. | |
| 6,379,631 B1 | 4/2002 | Wu | |
| 2002/0068012 A1 | 6/2002 | Platt, Jr. et al. | |
| 2003/0235511 A1 * | 12/2003 | Jacobs et al. ................. | 422/28 |

FOREIGN PATENT DOCUMENTS

| | | |
|---|---|---|
| EP | 0774263 B1 | 3/2003 |
| EP | 1 210 952 B1 | 9/2006 |

OTHER PUBLICATIONS

Sawyer et al. "Chemistry for Environmetal Engineers", Copyright 1994, McGraw-Hill Publishers, 4th Edition, pp. 60-62.*
Ethicon, Inc., Pending U.S. Appl. No. 09/728,973, filed, Dec. 4, 2000 (ASP-7).
Ethicon, Inc., Pending U.S. Appl. No. 09/975,714, filed Oct. 11, 2001 (ASP-41).
Ethicon, Inc., Pending U.S. Appl. No. 09/474,142, filed Dec. 29, 1999 (JJM-522).
Ethicon, Inc., Pending U.S. Appl. No. 09/474,285, filed Dec. 29, 1999 (JJM-523).

* cited by examiner

*Primary Examiner*—Gladys JP Corcoran
*Assistant Examiner*—Sean E. Conley

(57) ABSTRACT

A chemical vapor sterilization process is enhanced by controlling the temperature of a diffusion path between a vaporizer and a sterilization chamber so as to condense and then re-vaporize at least a portion of the vapor.

6 Claims, 7 Drawing Sheets

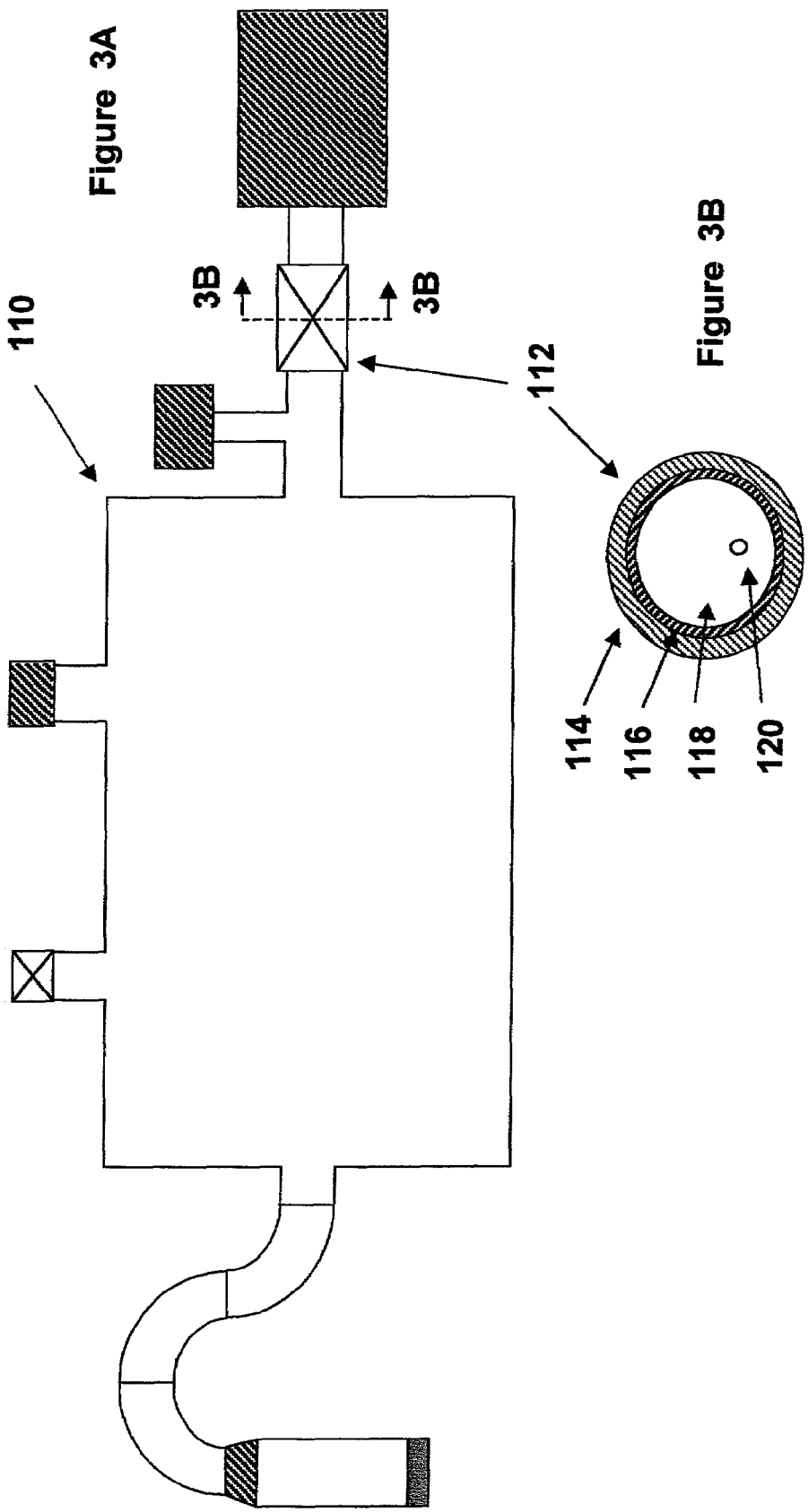

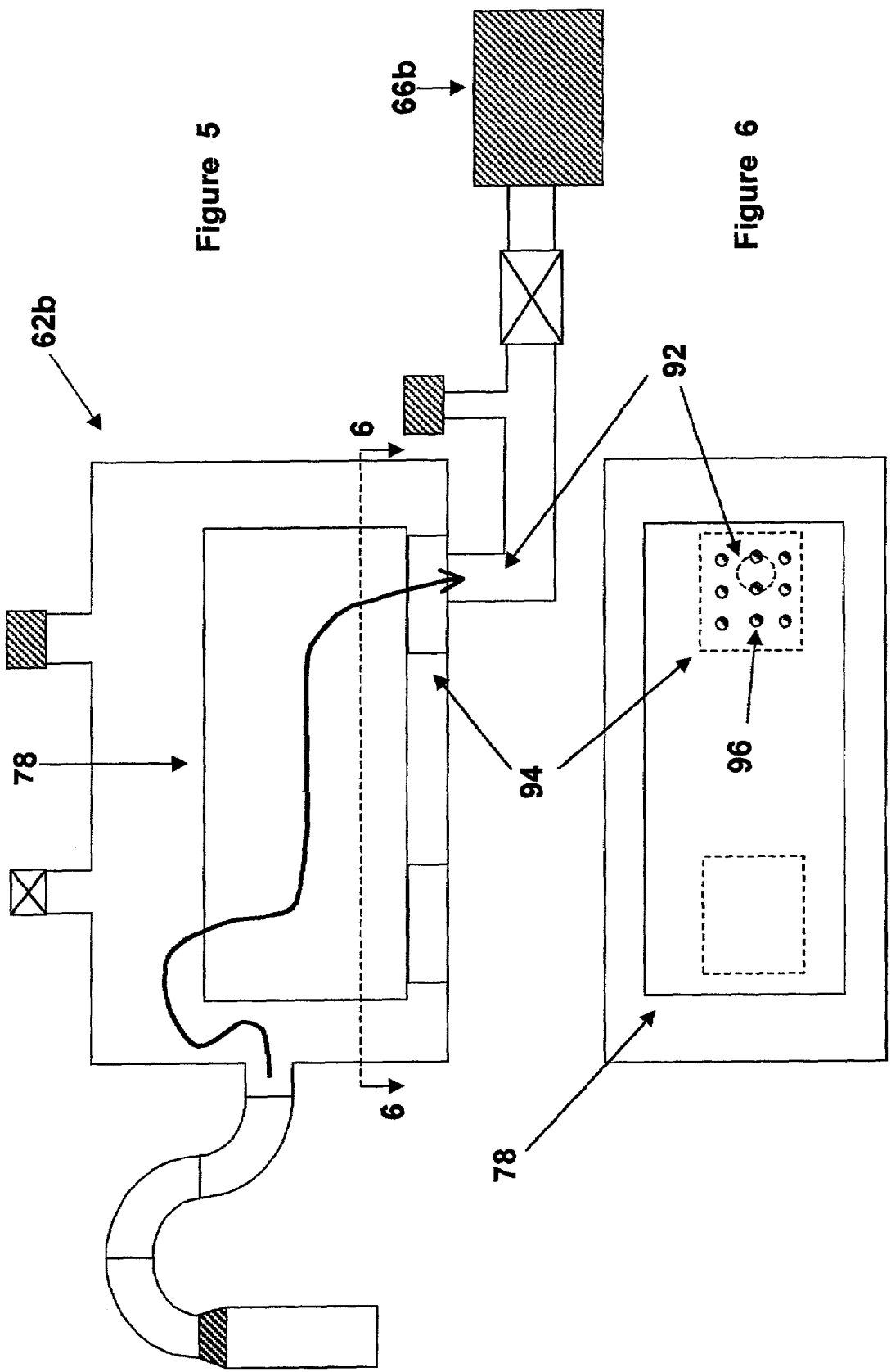

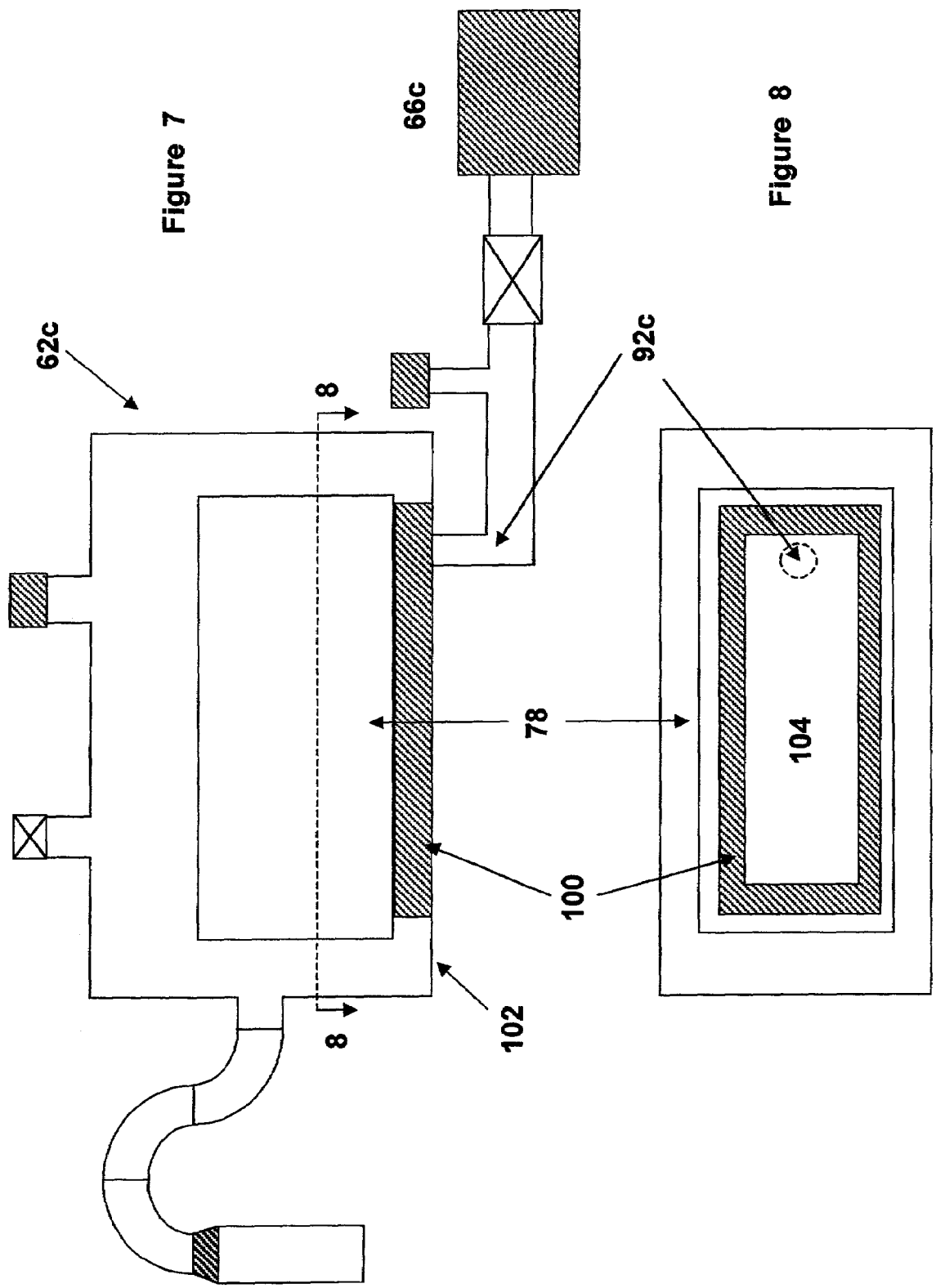

STERILIZER WITH RESTRICTOR

FIELD OF THE INVENTION

The invention relates to sterilization of articles, and more particularly to sterilization of articles which involves the step of evacuating a sterilization chamber vaporizing a liquid chemical sterilant solution.

BACKGROUND OF THE INVENTION

It is known to sterilize articles with a vaporized chemical sterilant, such as hydrogen peroxide, peracetic acid and glutaraldehyde. Wu et al. U.S. Pat. No. 6,365,102, incorporated herein by reference, describes a hydrogen peroxide/gas plasma sterilization system comprising a vacuum chamber, source of hydrogen peroxide vapor and a source of RF energy to create a plasma. Such systems marketed under the name STERRAD® are available from Advanced Sterilization Products division of Ethicon, Inc. in Irvine, Calif.

Jacobs et al., U.S. Pat. No. 6,325,972 found that when the water has a higher vapor pressure then the sterilant component of the solution, such a solution of hydrogen peroxide, that by controlling the temperature and pressure at which the solution is vaporized the water can be preferentially drawn off from the solution to increase the concentration of the sterilant in the solution. If the water is exhausted from the system during this process it leaves a higher concentration of the sterilant in the system. The higher concentration of sterilant during the phase in which the vapor phase sterilant contacts articles to be sterilized leads to increased efficiency in the sterilization process.

SUMMARY OF THE INVENTION

A sterilization system according to the present invention comprises a sterilization chamber, a vaporizer connected to the chamber, and a vacuum pump connected to the chamber. A valve and an orifice plate having an orifice therethrough are disposed between the pump the chamber. The orifice allows a slow, controlled pump down of the chamber during vaporization of a liquid sterilant solution to allow selectively drawing off a water fraction thereof thereby increasing the concentration of the sterilant solution.

Preferably, the orifice plate and the valve are disposed in parallel to each other. A second valve can be provided in series with the orifice plate, and preferably both the valve and the second valve have good shut-off capability. Alternatively, the orifice plate and the valve can be disposed in series.

Preferably, the valve is a throttle valve. It is advantageous if the valve has both good throttle and shut-off capability.

In one aspect of the invention, the valve comprises a valve body having a valve seat and a valve member adapted to move toward the seat to close the valve and away from the seat to open the valve. The valve member itself forms the orifice plate and has the orifice therethrough.

A method of furnishing concentrated hydrogen peroxide vapor to an article according to the present invention comprises the steps of: placing the article into a chamber containing an inner atmosphere; placing a solution comprising hydrogen peroxide and water into fluid communication with the chamber, said solution having a ratio of hydrogen peroxide to water; evacuating the chamber to lower pressure therein; vaporizing the solution in the inner atmosphere to form water vapor and hydrogen peroxide vapor; controlling the rate of evacuation of the chamber so as to selectively draw water vapor from the chamber to increase a ratio of hydrogen peroxide to water in the chamber, wherein the rate evacuation is controlled by evacuating the chamber through an orifice in an orifice plate; and contacting the article with the hydrogen peroxide vapor.

Preferably, during an initial portion of the step of evacuating the chamber atmosphere being evacuated can bypass the orifice and during a later portion of the step of evacuating the chamber, in which water vapor is being selectively drawn from the chamber, the atmosphere being evacuated from the chamber can not bypass the orifice.

The step of controlling the rate of evacuation of the chamber preferably maintains the solution at a pressure below the vapor pressure of the water in the solution and above the vapor pressure of the hydrogen peroxide in the solution. For efficient vaporization, the step of controlling the rate of evacuation of the chamber maintains the solution at a pressure below the vapor pressure of the solution.

The method can further comprise controlling the temperature of the vaporizer to control the rate of vaporization.

BRIEF DESCRIPTION OF THE DRAWINGS

FIG. 3A is a block diagram of an alternative embodiment of a sterilization system according to the present invention.

FIG. 3B is a sectional view taken along lines 3B—3B of FIG. 3A;

FIG. 5 is a block diagram of an alternate embodiment of a sterilization system according to the present invention;

FIG. 6 is a section view taken along lines 6—6 of FIG. 5;

FIG. 7 is a block diagram of an alternate embodiment of a sterilization system according to the present invention; and FIG. 8 is a section view taken along lines 8—8 of FIG. 7

DETAILED DESCRIPTION

Figure 1:
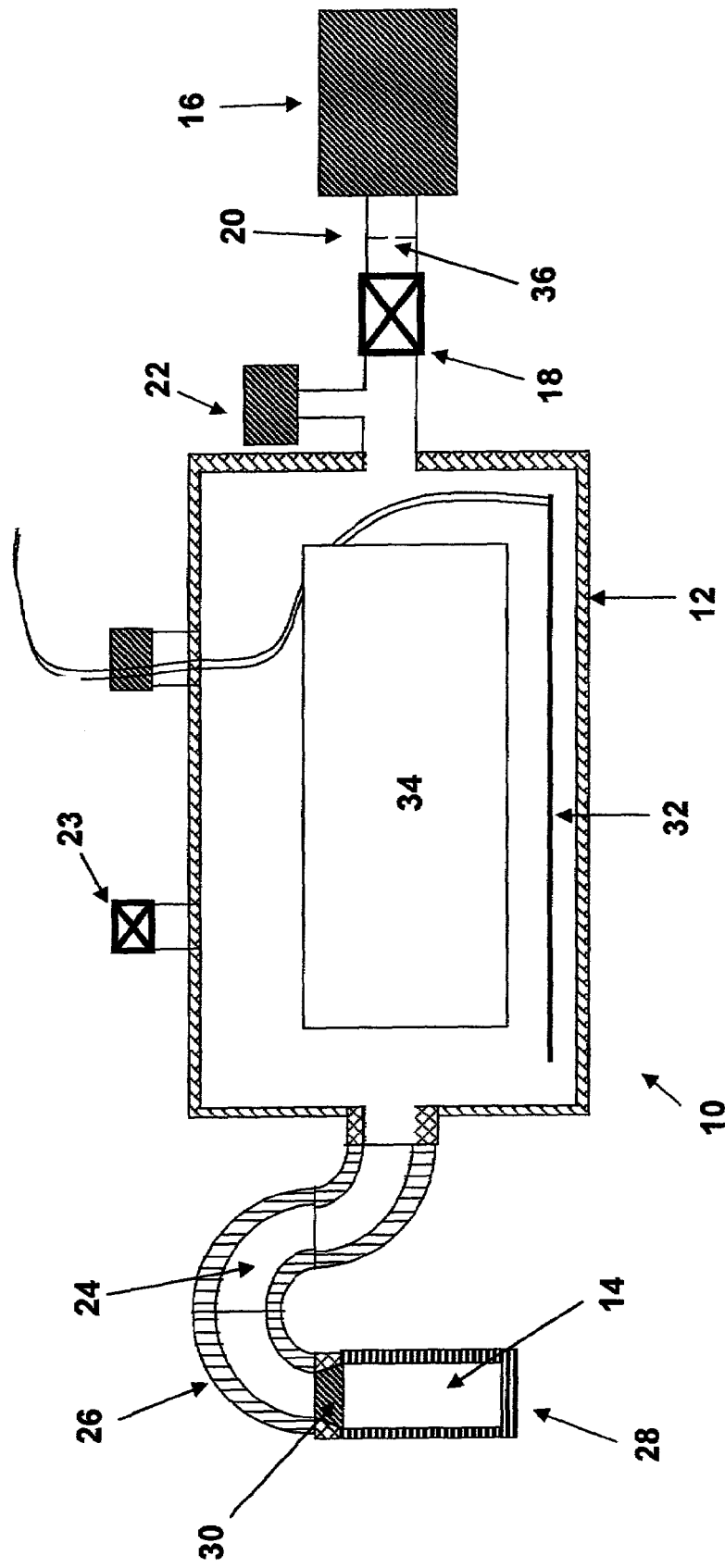
FIG. 1 is a block diagram of a sterilization system according to the present invention.
Figure 2:
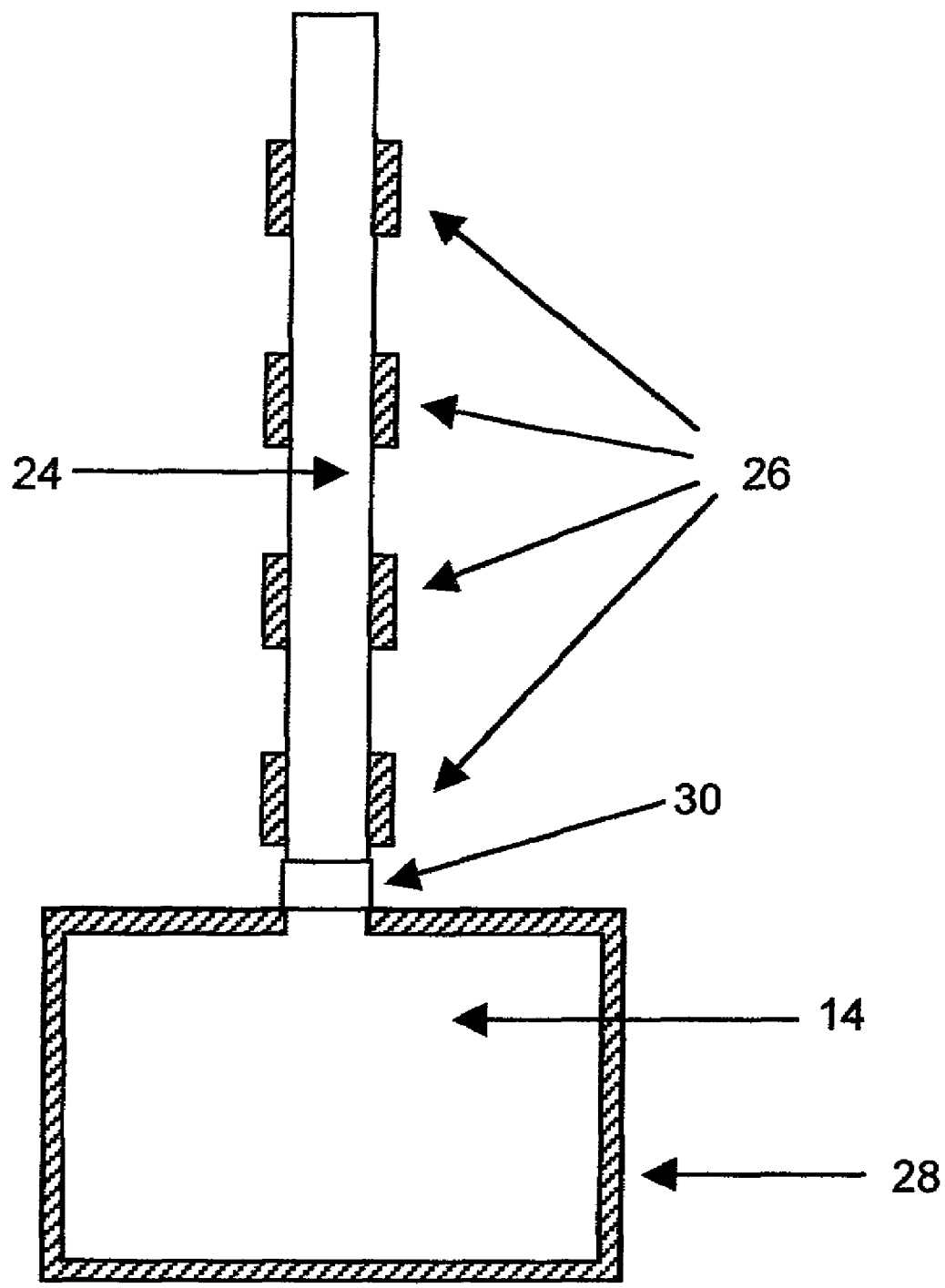
FIG. 2 is a block diagram of a vaporizer and diffusion path of the sterilization system of FIG. 1.

FIG. 1 shows in block diagram form a sterilization system 10 comprising a sterilization chamber 12, a vaporizer 14, and a vacuum pump 16. The vacuum pump is capable of drawing a vacuum on the chamber, preferably as low as 0.5 torr. Between the vacuum pump 16 and the chamber 12, is preferably located at throttle valve 18 and optionally an orifice plate 20. The throttle valve 18 preferably also has good shut-off capability. A pressure gauge 22, preferably located adjacent to the throttle valve 18, shows the vacuum in the chamber 12. A vent valve 23 employing a HEPA antimicrobial filter allows clean sterile air to enter the chamber 12. The vaporizer 14 connects to the chamber 12 by means of an elongated diffusion path 24. Turning also to FIG. 2, the diffusion path 24 incorporates temperature control elements 26 to control the temperature along the diffusion path 24.

Vaporizers suitable for vaporizing a liquid sterilant such as hydrogen peroxide solution are known in the art. Kohler et al. U.S. Pat. No. 6,106,772 and Nguyen et al. U.S. patent application Ser. No. 09/728,973 filed Dec. 10, 2000, both incorporated herein by reference, illustrate vaporizers suitable for the present application. In its simplest for the vaporizer can comprise a small chamber into which the liquid hydrogen peroxide solution is injected. The low pressure in the vaporizer caused by the vacuum in the chamber causes the hydrogen peroxide solution to vaporize.

Preferably, the vaporizer 14 itself incorporates heating elements 28 which control the temperature in the vaporizer to optimize the vaporization process.

Preferably, where the vaporizer 14 connects to the diffusion path 24 some form of thermal insulation 30 provided at the interface so that the high temperatures of the vaporizer 14 will not unduly affect the temperature in the diffusion path 24. The vaporizer 14 and diffusion path 24 are preferably formed of aluminum; the thermal insulation 30 can take the form of a polyvinyl chloride (PVC) joint connecting the two together.

Further, it is preferable to include a heater 32 inside the chamber 12, preferably near a lower portion of the chamber 12 for revaporizing condensed hydrogen peroxide inside the chamber 12.

The chamber 12 preferably includes a mechanism (not shown) to create a plasma therein. Such mechanism can include a source of radio or low frequency energy as described by Jacobs et al. U.S. Pat. No. 4,643,867, or by Platt, Jr. et al. in published U.S. Application Document No. 20020068012, both of which are incorporated herein by reference.

The present invention achieves its beneficial effect by allowing some of the hydrogen peroxide which is vaporized out of solution in the vaporizer 14 to condense onto the diffusion path 24. After most of the hydrogen peroxide solution has vaporized, the temperature control elements 26 raise the temperature of the diffusion path to allow the condensed hydrogen peroxide to re-vaporize. Water has a higher vapor pressure than hydrogen peroxide, thus hydrogen peroxide in the vapor condenses more easily than water. Thus, the material which condenses in the diffusion path will have a higher concentration of hydrogen peroxide than the starting concentration of the hydrogen peroxide solution in the vaporizer 14.

The temperature control elements 26 in simple form can comprise mere electric resistance heaters. In such case, the low ambient temperature of the diffusion path 24 provides the low temperature for condensing hydrogen peroxide thereon, and the control elements 26 later heat the diffusion path 24 to re-vaporize the now more highly concentrated hydrogen peroxide from the diffusion path 24. Because the vapor pressure of hydrogen peroxide drops with lower temperatures, lower initial temperatures in the diffusion path 24 allows a lower pressure in the chamber 24 without subsequently preventing the condensation of hydrogen peroxide in the diffusion path. Lower chamber pressures promote system efficiency and thus, the temperature control elements 26 can further comprise a chilling component to lower the temperature of the diffusion path below ambient. Suitable chilling components include thermoelectric coolers or a typical mechanical refrigeration system. In such case, the diffusion path 24 would be first chilled, preferably to about 10° C., and then some time after vaporization has begun or even after it has completed, the diffusion path 24 is then heated, preferably up to 50° C. or 110° C.

When vertically oriented as in FIG. 2, the diffusion path 24 can potentially cause the vaporizing sterilant to condense in cooler regions between the temperature control elements 26 and then re-vaporize as it passes the temperature control element 26.

The following example illustrates the benefits of controlling the heat in the diffusion path.

EXAMPLE 1

The efficacy tests were conducted by placing a CSR-wrapper tray (3.5"×10"×20") consisting of representative medical devices and test lumens in a 20-liter aluminum chamber (4.4"×12"×22"). A one-inch stainless steel wire inoculated with at least $1\times10^6$ Bacillus stearothermophilus spores was placed in the center of each of the test lumens. The effects with and without temperature control of the diffusion path were investigated with both a TEFLON, poly(tetrafluoroethylene)lumen having an internal diameter of 1 mm and a length of 700 mm, and a stainless steel lumen having an internal diameter of 1 mm, and a length of 500 mm. All lumens were open at both ends. Each of the samples were subjected to a sterilization cycle in a 20 liter vacuum chamber, which was held at 40° C. and 3 torr for 5 minutes. 1.44 ml of a 59% solution of hydrogen peroxide in water was injected at atmospheric pressure into the vaporizer which was held at 60° C. The 5 minute clock then started and the chamber was pumped down to 3 torr, which took less than one minute. In one case the diffusion path 24 had an initial temperature of 30° C. for the first minute while the chamber was evacuated to 3 torr and was then heated to 50° C. to release the condensed peroxide from the diffusion path into the chamber for the remainder of the cycle while pressure was maintained at 3 torr. In the other case, the diffusion path was held at 50° C. throughout the cycle. By maintaining the diffusion path at 50° C., no or little peroxide was retained in the diffusion path. Sterilization effectiveness was measured by incubating the test samples in growth media at 55° C. and checking for growth of the test organism. Table 1 shows the results of these tests.

TABLE 1

| Lumen Type | ID & Length | 50° C. Diffusion Path Throughout Process | 30° C. Diffusion Path For One Minute Then increased to 50° C. |
|---|---|---|---|
| Teflon | 1 × 700 | 2/2 | 0/3 |
| Stainless Steel | 1 × 500 | 1/2 | 0/3 |

When the diffusion path temperature was maintained at high temperature throughout the process, all of the samples in the TEFLON lumen tested positive for bacteria growth, indicating failure of sterilization, and one of two samples in the stainless steel lumen tested positive. Under the same conditions, but with an initially lower temperature diffusion path which was heated starting one minute after the diffusion began, none of the samples tested positive. Condensing the peroxide in the diffusion path during the initial vaporization stage and then re-vaporizing the condensed peroxide from the diffusion path into the chamber greatly enhance the efficacy.

Additional efficiencies can be achieved by alternating cool and warm regions in the diffusion path 24 as primarily illustrated in FIG. 2. The temperature control elements 26, in simple form heating elements, are spaced apart from one another. Also, preferably, the diffusion path 24 is vertical in this respect. As the hydrogen peroxide solution vaporizes and passes through the diffusion path 24, it is thought that it may alternately condense and re-vaporize as it passes over the heated and unheated sections of the diffusion path 24.

The diffusion path could alternatively comprise alternating heating and cooling elements.

The heater 32 within the chamber 12 acts similarly to the heating of the diffusion path 24. By controlling the heater 32 temperature, the peroxide can be first condensed on the heater 32 and then re-vaporized into the chamber 12 to concentrate the peroxide.

A preferred cycle would be a modification of a cycle described in the Wu et al. U.S. Pat. No. 6,365,102, incorporated herein by reference. A series of pre-plasma energy additions with venting in-between dries moisture from the chamber 12. A vacuum is then drawn upon the chamber 12 and the hydrogen peroxide solution injected into the vaporizer 14. Alternatively, the peroxide solution can also be injected at atmospheric pressure. Some of the vaporizing solution condenses upon the cool diffusion path 24. After a time sufficient for most or all of the hydrogen peroxide solution to vaporize from the vaporizer 14, the diffusion path 24 is warmed by the temperature control elements 26 and the condensed hydrogen peroxide solution re-vaporizes. At about this time, the throttle valve 18 is closed and the pump 16 turned off to seal the chamber 12. Much of the water fraction of the hydrogen peroxide solution has thus been drawn out of the chamber 12 by the vacuum pump 16 and the remaining hydrogen peroxide solution which re-vaporizes from the diffusion path 24, or from the heater 32 in the chamber 12 if present, is of a higher hydrogen peroxide concentration than the starting solution. Preferably, a computer based control system (not shown) controls the functions of the process for ease and repeatability.

The hydrogen peroxide vapor thus produced contacts an article 34 or articles 34 in the chamber 12 and effects sterilization thereof. If those articles 34 have diffusion restricted areas, such as long, narrow lumens, it may be preferable to then vent the chamber 12 and allow clean sterile air therein to drive the hydrogen peroxide vapor deeper into the diffusion restricted areas. Then the chamber 12 is again subjected to vacuum and an additional injection of hydrogen peroxide, preferably with the heating sequence on the diffusion path, is repeated. After a time period sufficient to effect sterilization of the article 34, preferably with a six-log reduction in challenge organisms such as *Bacillus stearothermophilus*, a plasma is lit within the chamber 12, thereby enhancing the sterilization and breaking down the hydrogen peroxide into water and oxygen.

The orifice plate 20 can enhance the effect of concentrating the hydrogen peroxide during its vaporization. As described in the Lin et al. U.S. Pat. No. 5,851,485, incorporated herein by reference, a controlled or slow pump-down of the chamber 12 initially draws off more water than hydrogen peroxide from solution as the water has a higher vapor pressure, thereby leaving a higher concentration hydrogen peroxide behind. Controlling the pump-down can be difficult as vacuum pumps generally do not throttle back well and throttle valves in such service are difficult to control and expensive. By placing the orifice plate 20 in the flow path to the pump 16, the amount of atmosphere from the chamber 12 exhausted by the pump 16 is limited, and by selecting a proper size orifice 36 in the plate 20 can be controlled to a rate which effectively concentrates hydrogen peroxide in the chamber 12.

Figure 3:
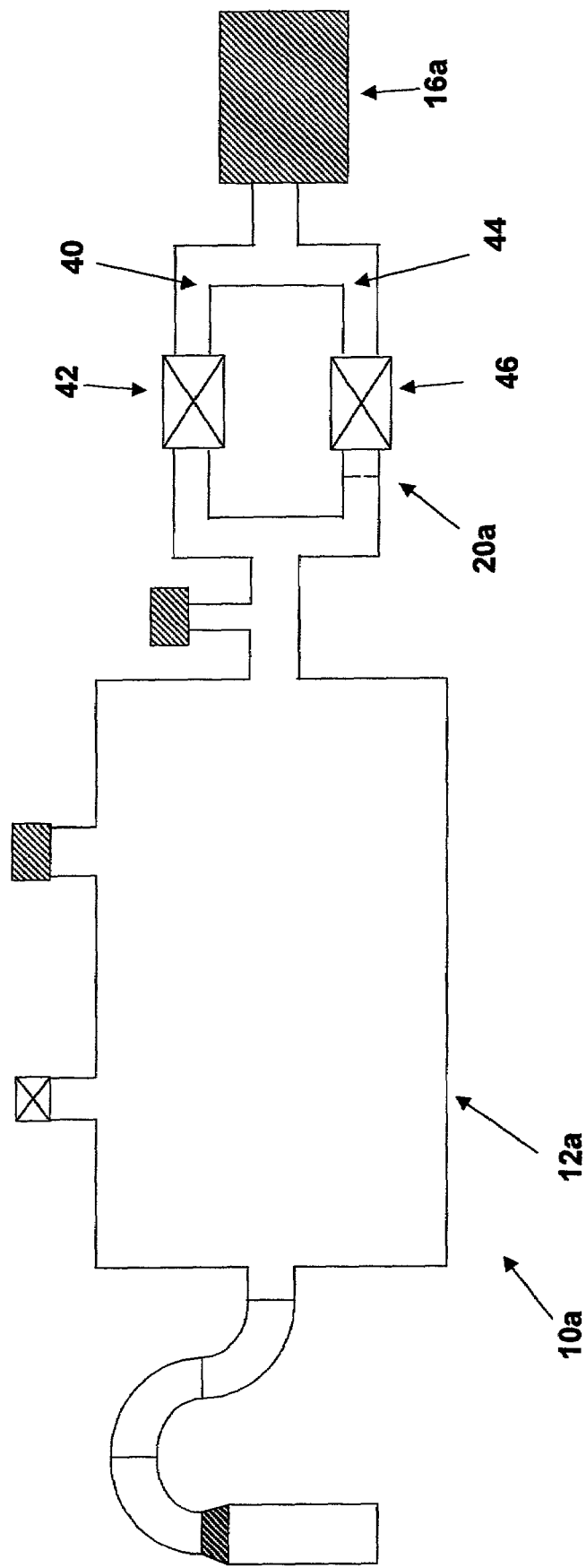
FIG. 3 is a block diagram of an alternate embodiment of a sterilization system according to the present invention.

Turning also to FIG. 3, a system 10a, similar in most respects to the system 10 of FIGS. 1 and 2, with like part numbers denoted with an "a" appended thereto, also incorporates an orifice plate 20a. However, to allow a quick pump-down of the chamber 12a, yet retain the controlled pump-down benefits of the orifice plate 20a, it incorporates two path ways from the pump 16a to the chamber 12a. A first pathway 40 contains a throttle valve 42 and a second pathway 44 contains a throttle valve 46 and the orifice plate 20a. Thus, during initial pump-down the first throttle valve 42 is open leaving the pump 16a freely connected to the chamber 12a. As the chamber 12a approaches the vapor pressure of water, the first throttle valve 42 is closed thereby forcing the pump 16a to evacuate through the orifice plate 20a and thus draw out of the chamber 12a at a slower, controlled rate more conducive to preferentially drawing water out of the hydrogen peroxide solution and out of the chamber 12a.

Turning also to FIGS. 3A and 3B, a system 110 similar to that of FIG. 1 is shown. Here, rather than use two paths as in the system 10a of FIG. 3, a valve 112 comprises a valve body 114, a valve seat 116 and a valve element 118, such as a butterfly disc, plug or the like. An orifice 120 is provided through the valve element. Thus, when the valve 112 is open evacuation can occur quickly, and when the valve 112 is closed it can occur more slowly.

Figure 4:
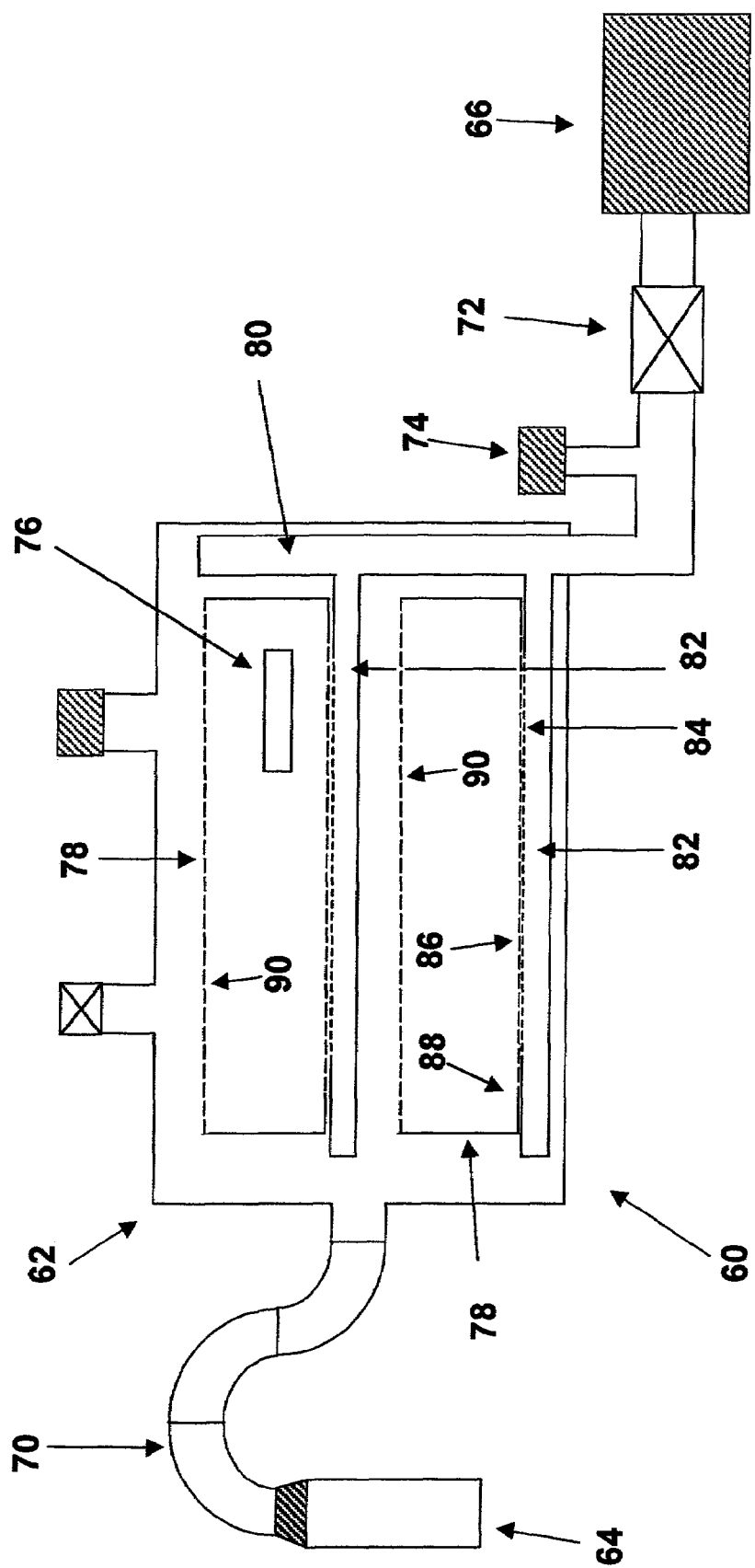
FIG. 4 is a block diagram of an alternate embodiment of a sterilization system according to the present invention.

Turning now to FIG. 4, while highly concentration of the sterilizing vapor is helpful in achieving sterilization efficiency and efficacy, getting the vapor into contact with the items to be sterilized is also a concern. Typically, the low pressures (0.5 torr to 10.0 torr) inside of a chamber 12 promotes quick diffusion of the sterilant vapor to all areas therein.

FIG. 4 illustrates a sterilization system 60 comprising a chamber 62 having a vaporizer 64, vacuum pump 66 and vent 68 connected thereto. Preferably, an elongated, temperature controlled diffusion path 70 as previously described connects the vaporizer 64 to the chamber 62. A throttle valve 72 and pressure gauge 74 are provided at the pump 66.

Articles 76 to be sterilized are placed into trays or containers 78. Two types of packaging are commonly used in preparing articles 76 for sterilization. In one, the articles 76 are placed into a tray having a plurality of openings therein, and the tray is then wrapped with a material such as CSR wrap which passes sterilizing gases and blocks contaminating microorganisms. Such a tray is described in the Wu, U.S. Pat. No. 6,379,631, incorporated herein by reference. An alternative package comprises a sealable container with several ports, preferably on top and bottom surfaces thereof, with each of the ports covered by a semi-permeable membrane which passes sterilizing gases and blocks admission of contaminating microorganisms. Such a container is described in Nichols U.S. Pat. No. 4,704,254, incorporated herein by reference. The first type of packaging is typically called a "tray" and the second a "container." However, the term "container" as used herein is meant to refer to any container, packaging or enclosure suitable for containing articles to be sterilized in a chemical vapor environment.

The pump 66 connects to the chamber 62 via an exhaust manifold 80. The manifold 80 comprises one or more shelves 82 for supporting and receiving one or more containers 78 and which connect fluidly through the throttle valve 72 to the pump 66. An opening, or preferably a plurality of openings 84 on the upper surfaces of the shelves 82 allow the pump 66 to draw atmosphere within the chamber 62 through the openings 84, through the manifold 80 and out through the pump 66.

The containers 78 preferably have openings 86 on a lower surface 88 thereon and additional openings 90 on at least one other surface. When the containers 78 are placed on the shelves 82 atmosphere being exhausted by the pump 66 is drawn in part through the openings 90 into the container 78, through the container into contact with the article or articles 76 therein and then out through the openings 86 into the manifold 80 through the openings 84 therein. When the atmosphere being so exhausted contains a sterilizing gas it enhances its penetration into the containers 78 and into contact with the articles 76 therein.

Sterilizing gases are so exhausted during the previously described cycle as the sterilant solution is vaporizing and immediately before the second admission of hydrogen peroxide. Such a cycle can also further provide a pump-down after some period of diffusion. After admitting the sterilant vapor the chamber 62 pressure rises slightly due to the presence of additional gas therein, typically from about 0.5 torr to about 10 torr. Higher pressures are as efficient with higher load and chamber temperatures.

Turning also to FIGS. 5 and 6, an alternative design (in which like part numbers to those of the design of FIG. 4 are designated with a "b" appended thereto) replaces the manifold 80 of the design of FIG. 4 with a simple port 92. The port 92 is covered by a support 94 for the container 78, the support 94 having a plurality of openings 96 therethrough so that the chamber 62b is in fluid communication with the pump 66b through the container 78, the support 94 and the port 92. The support 94 can be removable.

Turning also to FIGS. 7 and 8 (in which like part numbers to those of the designs of FIGS. 4 to 6 are designated with a "c" appended thereto) shows a support 100 resting on a surface 102 in the chamber 62c through which penetrates the port 92c. The support 100 surrounds the port 92c. Thus, most or all of the atmosphere being exhausted by the pump 66c passes through the container 78 into a space 104 formed between the container 78, the support 100 and the surface 102 and then onto the pump 66c through the port 92c.

What is claimed is:

1. A method of furnishing concentrated hydrogen peroxide vapor to an article comprising the steps of:
    placing the article into a chamber containing an inner atmosphere;
    placing a solution comprising hydrogen peroxide and water into fluid communication with the chamber, said solution having a ratio of hydrogen peroxide to water;
    evacuating the chamber to lower pressure therein;
    vaporizing the solution in the inner atmosphere to form water vapor and hydrogen peroxide vapor;
    controlling the rate of evacuation of the chamber so as to selectively draw water vapor from the chamber to increase a ratio of hydrogen peroxide to water in the chamber, wherein the rate evacuation is controlled by evacuating the chamber through an orifice in an orifice plate; and
    contacting the article with the hydrogen peroxide vapor.

2. A method according to claim 1 wherein during an initial portion of the step of evacuating the chamber atmosphere being evacuated can bypass the orifice and during a later portion of the step of evacuating the chamber, in which water vapor is being selectively drawn from the chamber, the atmosphere being evacuated from the chamber can not bypass the orifice.

3. A method according to claim 2 wherein the orifice is formed in a valve member located in valve between the chamber and a vacuum pump which evacuates the chamber, and wherein the step during the initial portion of the step of evacuating the chamber the valve is not closed and wherein during the later portion of the step of evacuating the chamber the valve is closed and the chamber is evacuated through the orifice through the valve member.

4. A method according to claim 1 wherein the step of controlling the rate of evacuation of the chamber maintains the solution at a pressure below the vapor pressure of the water in the solution and above the vapor pressure of the hydrogen peroxide in the solution.

5. A method according to claim 4 wherein the step of controlling the rate of evacuation of the chamber maintains the solution at a pressure below the vapor pressure of the solution.

6. A method according to claim 1 wherein the solution is located in a vaporizer and the method further comprises controlling the temperature of the vaporizer to control the rate of vaporization.

* * * * *